United States Patent [19]

Rinik et al.

[11] Patent Number: 4,649,556
[45] Date of Patent: Mar. 10, 1987

[54] METHOD AND APPARATUS FOR THE "ON-LINE", NONDESTRUCTIVE MEASUREMENT AND CONROL OF GRAIN SIZE IN MATERIALS

[75] Inventors: Christine Rinik, Arlington, Mass.; Jerome B. Cohen, Glencoe; John E. Hilliard, Evanston, both of Ill.

[73] Assignee: Northwestern University, Evanston, Ill.

[21] Appl. No.: 584,115

[22] Filed: Feb. 27, 1984

Related U.S. Application Data

[63] Continuation-in-part of Ser. No. 422,654, Sep. 24, 1982.

[51] Int. Cl.$^4$ ............................................. G01N 23/20
[52] U.S. Cl. .......................................... 378/71; 378/73
[58] Field of Search ..................................... 378/71, 73

[56] References Cited

U.S. PATENT DOCUMENTS

| | | | |
|---|---|---|---|
| 2,958,777 | 11/1960 | Sieswerda | 378/86 |
| 3,144,556 | 8/1964 | van Tillo | 378/86 |
| 3,564,251 | 2/1971 | Youmans | 378/59 |
| 4,076,981 | 2/1978 | Sparks | 378/71 |

OTHER PUBLICATIONS

"X-Ray Diffraction Procedures", Klug et al., John Wiley and Sons Inc., New York, 1954, p. 88.

*Primary Examiner*—Craig E. Church
*Attorney, Agent, or Firm*—Welsh & Katz, Ltd.

[57] ABSTRACT

A method and apparatus for the "on-line", nondestructive measurement and control of grain size in various materials, such as steel, powders, ceramics, semiconductors, and crystalline polymers. A substantially monochromatic beam of X-rays is directed at the material as it moves relative to a predetermined measuring station. The incident X-ray beam has a predetermined cross-sectional area so that over a plurality of time intervals a plurality of corresponding non-overlapping area segments are irradiated. The time-integrated intensity of diffracted radiation from each non-overlapping area segment is measured and the relative variance of the intensity measurements within the total area irradiated is determined. The relative variance of the measured intensities is then used to determine the grain size of the products which is generally reported as the mean grain diameter, weighted with respect to volume.

19 Claims, 4 Drawing Figures

METHOD AND APPARATUS FOR THE "ON-LINE", NONDESTRUCTIVE MEASUREMENT AND CONTROL OF GRAIN SIZE IN MATERIALS

OTHER RIGHTS OF THE INVENTION

"The U.S. Government has rights in this invention pursuant to grant DMR 76-80847 from the National Science Foundation."

This application is a continuation in part of a pending application filed on Sept. 24, 1982, and has Ser. No. 422,654.

FIELD OF THE INVENTION

The present invention relates generally to the field of metallurgy and materials engineering and more specifically to a method and apparatus for the "on-line", nondestructive measurement and control of grain size in the fabrication of products such as steel, ceramics, semiconductors, and crystalline polymeric materials in the form of sheet, plate, strip, cylinders and bar stock. The invention can also be used for control of particle sizes in the production of abrasive materials and paint pigments and for particle size control in the mining industry.

DESCRIPTION OF PRIOR ART

The relationship between grain size and the mechanical properties of metals, ceramics, crystalline polymers, semiconductors and other materials has been known for many years. Tensile strength, yield strength, ductility, atomic diffusion characteristics and other physical properties can all be predictably influenced by proper grain size control carried out through a variety of known means including chemical, mechanical and thermal treatments. In one example in the manufacture of wrought steel products, the grain size of the metal is greatly influenced by the degree of deformation to which it is subjected and its cooling rate from hot working temperatures. In another example, the control of the size of abrasive particles, ranging from 0.05 μm to 500 μm in diameter, is critical to the polishing qualities of a batch of end product polishing material. Thus, it would be desirable to be able to make "on-line" grain size measurements, so that control of the aforementioned parameters could be utilized to achieve a desired grain size in the finished product.

Large manufacturers, such as steel mills, are not presently able to carry out "on-line" grain size measurement due to the practical limitations of present methods. Most often, grain size measurements are made with the aid of an optical microscope on polished and etched specimens selected from various portions of the finished product. ASTM Designation E-112 sets forth three procedures, known as the comparison, intercept (or Heyn), and planimetric (or Jeffries') procedures. Each procedure involves direct microscopic measurements or the observation and comparison of the microstructure of a sample to known standards, both of which are labor intensive and time consuming.

Steel mills and other materials processors are therefore often constrained to having grain size measurements made only after considerable manufacturing expense has already been incurred. For example, in the manufacture of metal strip or bar stock, partially solidified ingots are charged directly into soaking pits where they remain until reaching a uniform hot rolling temperature. The soaked ingots are reduced in cross-section to slabs or blooms by a primary roughing mill and then put in a reheat furnace prior to hot rolling. Hot rolling to strip or bar stock is usually carried out in a multi-stand tandem hot mill. Thus, the first practical opportunity for grain size measurement employing conventional microscopy occurs after hot rolling and cool down. In this form one can remove representative samples for grain size measurement. This can often result in the need for remedial heat treatment, diversion of the order or the generation of scrap.

While optical microscopy is by far the most common way of measuring the grain size of materials, another method employs x-ray diffraction which is also known in the art. This latter method of grain size measurement has been applied to both solid materials and to noncontiguous polycrystalline substances, such as, for example, powders of ionic salts (e.g., KCl). A substantially monochromatic beam of x-radiation, having a known wavelength, is directed at a predetermined number of locations on the surface of the polycrystalline specimen. At each location, some of the grains impinged by the incident x-ray beam are oriented so that certain of their crystallographic planes are in a diffracting position. Therefore, the crystallograhic planes are oriented with respect to the incident beam so as to satisfy Bragg's Law. When the number of grains so oriented with respect to the incident x-ray beam is small compared to the number of grains irradiated, the intensity of the radiation diffracted from the various locations closely follows a statistical frequency distribution known as Poisson's distribution. In an article entitled, "X-ray Measurement of Grain Size", 31, Journal of Applied Physics, 12, (1960), B. E. Warren disclosed a method for determining an approximate value of mean grain diameter in a noncontiguous polycrystalline powder of KCl, utilizing the aforementioned Poisson's frequency distribution model and idealizing the KCl grain shape as spherical. In Warren's method, the powder sample was held stationary with respect to the incident x-ray beam while the intensity of radiation diffracted by the (200) KCl diffracting planes was measured at each of various locations on the sample.

As will be understood by those skilled in the art, the diffracted intensity measurements disclosed by Warren represent the total number of counts registered by a suitable counter over the fixed period of time during which the sample was irradiated at a given location. Warren's method discloses that the polycrystalline sample is stationary with respect to the incident x-ray beam and that the sample "dwells" at each location while the diffracted x-ray intensity is measured. In the "on-line" measurement of grain size, for example, in a stream of flowing powders or in a multi-stand hot strip mill or a temper mill, the intended sample is generally moving at a high rate of speed, velocities of 1,500–3,500 ft./min. not being uncommon.

SUMMARY OF THE INVENTION

In accordance with the present invention, a method and apparatus are provided for the measurement of grain size in polycrystalline materials (such as metals, ceramics, semiconductors, polymers, or powders) while the material is in motion relative to a predetermined measuring station. An incident beam of substantially monochromatic x-radiation, having a predetermined wave length, is directed at the material as it moves relative to the measuring station at a known velocity.

The incident beam has a predetermined cross-sectional area so that over a series of predetermined time intervals, a plurality of corresponding, nonoverlapping area segments on the moving material are irradiated. The time-integrated intensity of radiation diffracted from a predetermined set of diffracting planes and corresponding to each area segment, is detected by suitable means such as a proportional counter. Finally, the relative variance of the time-integrated intensities corresponding to each of the nonoverlapping area segments in the total area irradiated is determined. The relative variance is then used to determine the grain size of the material which is generally expressed as a mean grain diameter, weighted by volume or area.

Once the mean grain diameter has been determined, corrective action can be taken if necessary. As mentioned, in a hot strip mill the grain size of the metal is greatly influenced by the temperature at which finish rolling and coiling occur, as well as the reduction taken by the various roll stands. Thus, the grain size can be effectively varied by controlling such parameters as slab reheat times and temperatures, the roll openings in the roughing and finishing mills, metal delivery and throughput rates and cooling by appropriately placed sprays. Such operations are already computer controlled in many modern steel plants so that the present invention can be readily interfaced with existing facilities for the control of grain size.

It is therefore a primary object of the present invention to provide a method and apparatus for the "on-line", nondestructive measurement of grain size.

It is another object of the invention to provide a method and apparatus for the measurement of grain size which can be carried out quickly so that such operating parameters as temperature, deformation, and cooling rate can be varied during the production of wrought products to control final grain size.

A feature of the present invention is that it permits the measurement of grain size in materials, such as metal products, while the material is moving at speeds of up to 1,500 to 3,500 feet per minute.

These and other objects and features of the present invention will become apparent from the following detailed description and accompanying drawings of which:

DETAILED DESCRIPTION OF THE INVENTION

Figure 1:
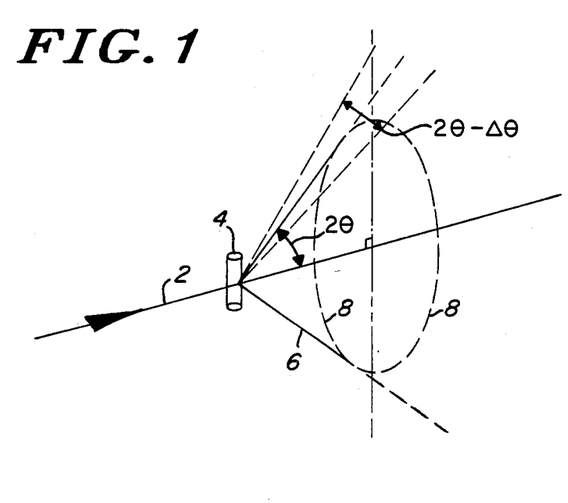
FIG. 1 is a schematic representation of x-ray diffraction produced by the Debye-Scherrer powder method.

The use of x-ray diffraction to study the geometry and structure of crystalline materials has been well known for many years. In one frequently used method, the Debye-Scherrer powder method, the sample generally comprises a large number of randomly oriented grains or crystal particles in solid form or in powder form. As shown in FIG. 1, when an x-ray beam 2 of substantially monochromatic radiation having a wave length $\lambda$, impinges on a powder sample 4, a portion of the total number of grains irradiated will be oriented in a diffracting position with respect to the incident beam 2. The diffracting, crystallographic planes form an angle $\theta$ with respect to the incident beam so as to satisfy Bragg's Law $\lambda = 2\,d\,\sin\,\theta$, where d=the spacing between diffracting planes.

If the grain size is very small with respect to the total volume of material irradiated, then a large number of grains will be in a diffracting position and the diffracted radiation forms the well known Debye-Scherrer diffraction cone 6, which has a substantially constant intensity about its perimeter 8 taken in a plane normal to the incident beam 2. (FIG. 1). However, when the grain size in the powder sample is relatively large with respect to the total volume of material irradiated, then only a small number of grains are in diffracting positions, and the intensity of diffracted radiation varies about the perimeter 8 of the Debye-Scherrer cone 6.

In many instances it is practical to measure the intensity of diffracted radiation over only a small portion of the perimeter 8 of the Debye-Scherrer cone 6. Thus, the variation in intensity produced by large grain size has, in the past, led to incorrect experimental results unless accounted for.

In accordance with the present invention, the aforementioned variation in intensity is used to determine the grain size in materials, such as metals, which are preferably in the form of a strip, plate, sheet, cylinders, bar, or powders as the material travels past a measuring station. At the measuring station the material is impinged by an incident x-ray beam that traces a plurality of non-overlapping irradiated area segments. The main grain diameter is derived from the relative variance in the statistical distribution of the time-integrated intensity of radiation diffracted from the area segments.

Figure 2:
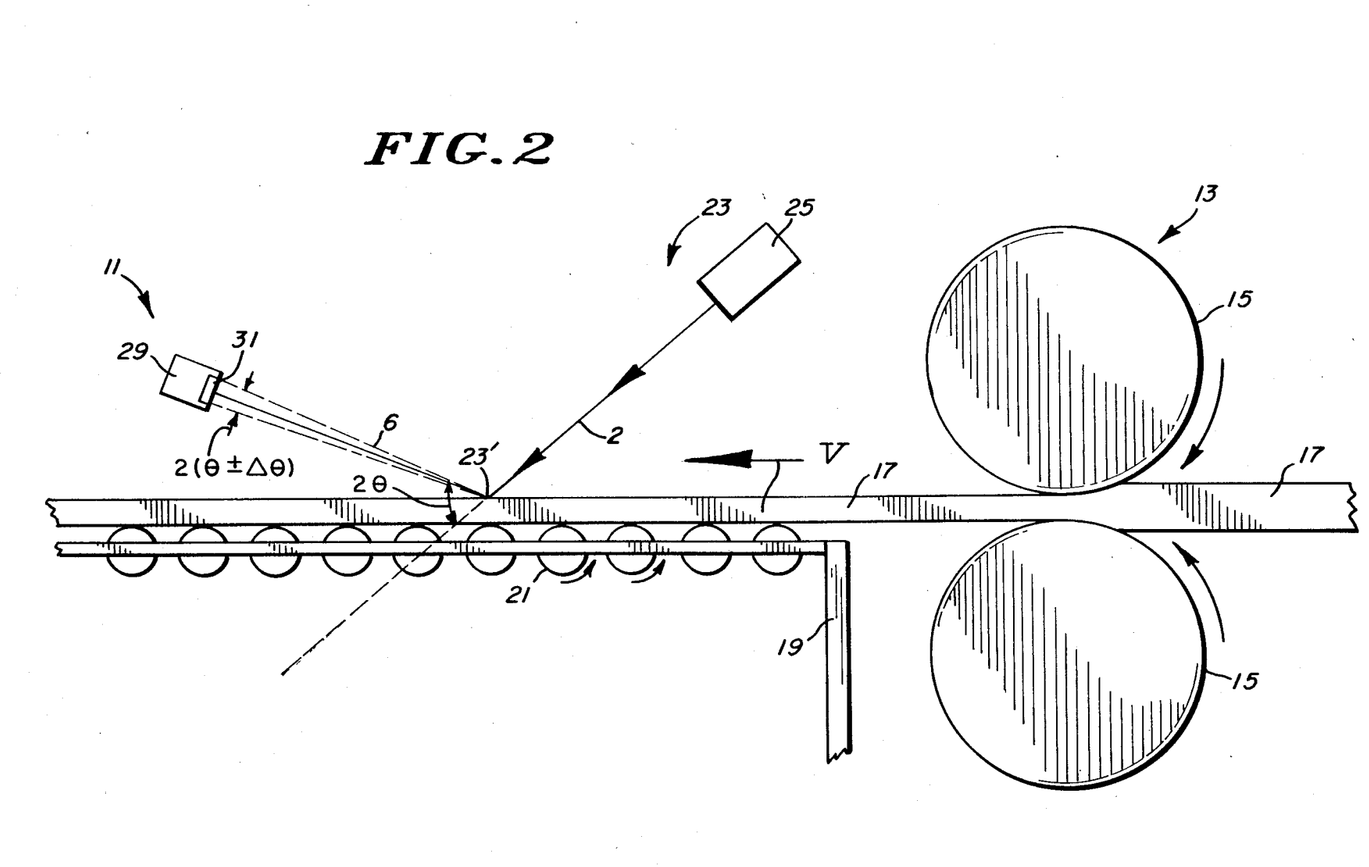
FIG. 2 is a schematic representation of a typical roll stand in a multi-stand tandem hot strip mill equipped with means for generating an incident beam for monochromatic x-radiation and means for detecting diffracted radiation suitable for carrying out the measurement of grain size in accordance with the present invention during rolling.

Referring now to FIG. 2 there is shown a schematic representation of an on-line grain size measuring apparatus for use in a steel plant and constructed in accordance with one invention embodiment indicated generally by reference numeral 11. The apparatus 11 is adapted for use in a steel plant in a multi-stand tandem hot strip mill, a typical roll stand 13 being represented in the drawing. The roll stand 13 includes a pair of working rolls 15 which rotate in opposite directions to elongate and reduce the thickness of a steel strip 17. As the strip 17 leaves the rolls 15 it is moved at a velocity V from right to left as viewed in FIG. 2, being carried on a transfer table 19. The transfer table 19 is equipped with a plurality of transfer rollers 21 that rotate to move the strip 17 to a subsequent roll stand for further reduction or to a coiler (not shown).

The grain size measuring apparatus of the invention 11 is located at a measuring station, generally indicated at 23, on the exit side of the roll stand 13, above the transfer table 19. The apparatus 11 includes means 25 for generating a substantially monochromatic incident beam of x-rays 2 having a predetermined wavelength $\lambda$, cross-sectional area $A_o$ and width $W_b$. The incident x-ray beam 2 impinges the steel strip 17 at a predetermined measuring point 23 on its surface.

Figure 3:
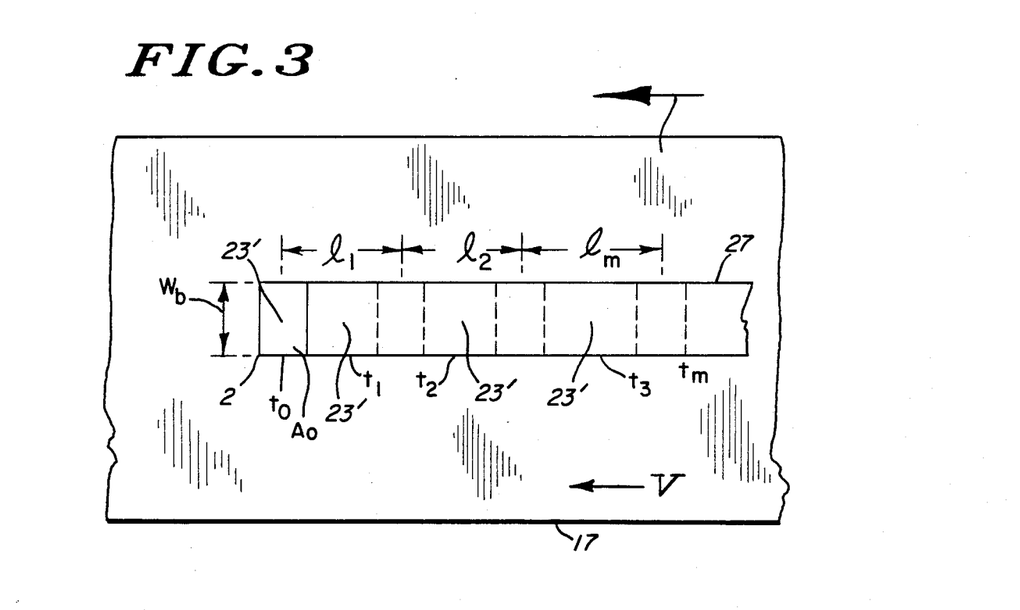
FIG. 3 is a schematic representation of a fragmentary, top view of FIG. 2 showing the nonoverlapping irradiation area segments traced on the surface of the strip by the incident x-ray beam.

As is schematically shown in FIG. 3, the incident x-ray beam 2 is stationary with respect to the measuring point 23 and thus irradiates a trace 27 on the surface of the sheet 17 as it travels past measuring point 23 at a velocity V. In an alternative embodiment the measuring station can be moved and the sheet 17 held fixed; therefore, the x-ray beam 2 moves and irradiates a trace along the surface of the fixed sheet 17. It is also possible to move both the measuring station and the sheet 17 to increase the processing rate.

In the illustrated embodiment of FIG. 3, after a predetermined time interval of $t_1-t_o$, the new position of the incident beam 2 and the measuring point 23 with respect to the strip 17 is shown by the broken lines about $t_1$. Thus, at time $t_1$ the sheet 17 has been irradiated over a length $l_1$ and an area segment, $A_1$, equal to the product of $W_b$ and $l_1$. It therefore follows that over a plurality of time intervals, a plurality of area segments, $A_n$, can be irradiated, each area $A_n$ being equal to the product of the width, $W_b$, of the incident beam 2, the velocity, V, of the strip 17 and the length of the time interval $t_n-t_{n-1}$. Of course, the total number of grains irradiated by the incident beam is a function of the depth of penetration of the beam as well as the irradiated area segments $A_n$ traced on the surface of the strip 17. As will be explained herein the depth of penetration influences the determination of grain size.

Referring now again to FIG. 2, it can be seen that the grain size measuring apparatus 11 of the invention also includes means 29 for measuring the intensity of x-radiation 6 diffracted by the grains in the steel strip 17 bounded by the trace 27 of area segments $A_n$ as the strip 17 moves past the predetermined measuring point 23 during the time interval $t_n-t_{n-1}$. In this sense the intensity measurement is said to be time-integrated and is preferably carried out by an x-ray counter.

X-ray counters operate on the principle that x-rays are capable of causing the ionization of certain gases or solids. For example, in the case of proportional counters the gases are contained in a chamber between a high voltage anode and cathode. Ionization of the gas causes a detectable current pulse to flow between the anode and cathode, the pulse rate being directly proportional to the intensity of radiation entering the ionization chamber. Thus, x-ray counters generally include circuitry for counting the pulses produced for a given time interval in order to establish the counting rate. The total count of pulses registered over a given time interval is, therefore, representative of the time-integrated intensity of radiation. Depending on intensity, counters generally require that they be operated for some minimum period of time in order to establish an accurate counting rate.

What is referred to herein as time-integrated intensity should be distinguished from the generally used terms intensity and integrated intensity. When used alone, the term intensity refers to the x-radiation flux at a given point in space, and is designated herein by the variable I. Similarly, diffracted radiation intensity will be designated herein Y. As is shown in FIG. 1, the Debye-Scherrer diffraction cone 6 forms an included angle of $2\theta$ with respect to the incident beam 2. The Debye-Scherrer cone 6 is, however, an idealized model and represents only the maximum intensity or highest flux radiation diffracted by the sample 4.

Figure 4:
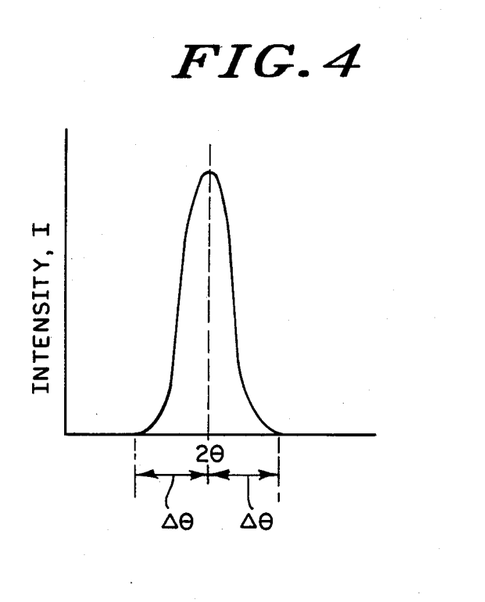
FIG. 4 is a graphical representation of diffracted radiation intensity as a function of twice the Bragg angle for a typical polycrystalline material.

FIG. 4 shows radiation intensity as a function of position about the Debye-Scherrer cone 6 along the arc $2\theta \pm \Delta\theta$, so that the distance from the irradiated portion of the sample 4 is constant. As mentioned, counters usually measure only a small segment of the periphery 8 of the Debye-Scherrer cone 6 so the intensity shown in FIG. 4 is representative of a "cross-section" of the cone 6, taken through a plane containing the axis of the incident beam 2. In FIG. 4 it can be seen that crystals having diffracting planes oriented at exactly the Bragg angle, $\theta$, produce the maximum intensity of diffracted radiation, but some radiation is still diffracted at an orientation of $\pm \Delta\theta$. Thus, the general term integrated intensity is often used to describe the cross-hatched area of the graph in FIG. 4, and for purposes of clarity will be referred to herein as the $\Delta\theta$-integrated intensity.

The $\Delta\theta$-integrated intensity can be measured in two ways. Preferably the counter 29 is of a type represented in FIG. 2, called a position sensitive proportional counter. This type of counter "sees" the entire $\Delta\theta$-integrated intensity as it is provided with a wide receiving slit 31 which permits the simultaneous detection of diffracted radiation over the entire range of $2\theta \pm \Delta\theta$. Appropriate electronics decode the angular position of each x-ray pulse. Some counters, however, are equipped with a relatively narrow receiving slit and are therefore capable of detecting only a narrow range about $2\theta$. It is then necessary to rotate the counter about the $2\theta$ position in order to determine the $\Delta\theta$-integrated intensity. In one form of the present invention, a measurement of the time-integrated peak intensity (i.e., precisely at $2\theta$) will suffice.

Having established means for irradiating a plurality of nonoverlapping area segments, $A_n$, and means for measuring the time-integrated intensity of diffracted radiation (either peak or $\Delta\theta$-integrated), the mean grain diameter in the subject material can be determined. In each area segment, the volume fraction of irradiated grains favorably oriented with respect to the incident beam so as to be in a predetermined diffracting position will be a relatively small number. The statistical distribution of grains so oriented can therefore be approximated by a known function, a Poisson distribution. Because the intensity of the diffracted radiation is directly proportional to the number of grains in a diffracting position, statistical analysis of the time-integrated intensities (either peak or $\Delta\theta$-integrated) can be used to determine grain size. In a contiguous polycrystalline material the relative variance of the time-integrated intensity of diffracted radiation due to the effect of grain size is directly proportional to the ratio of the second to the first statistical moment of the volumetric distribution of irradiated grains in the samples. Or, as written in algebraic form:

$$\frac{\sigma_{gs}^2(Y_p)}{\overline{Y}_p^2} = K_1 \frac{\mu'_2(v)}{\mu'_1(v)} \frac{\sigma_{gs}^2(Y_p)}{\overline{Y}_p^2}$$

= relative variance of diffracted x-ray intensities, $Y_p$, due to grain size;

v = the volume of a grain;

$K_1$ = a constant determined by x-ray operating parameters, explained more fully herein; and $\mu'_n(v)$ = the nth statistical moment of v about the origin.

The above expression, however, assumes that the depth of penetration of the x-rays in the sample is large with respect to grain size so that the relative variance of diffracted intensity is created by a volume fraction of irradiated grains. If the depth of x-ray penetration from the incident beam is small compared with the grain size (i.e. less than or equal to the mean grain diameter), then the relative variance is due primarily to the grains which intersect the surface of the metal specimen so that the relative variance can be algebraically expressed:

$$\frac{\sigma_{gs}^2(Y_p)}{\overline{Y_p}^2} = K_2 \frac{\mu'_2(a)}{\mu'_1(a)}$$

$\mu'_1(a)$ and $\mu'_2(a)$ being, respectively, the first and second statistical moments of the distribution of the areas of the irradiated grains intersecting the surface of the specimen. Once the moment ratio for either the volumetric or area distributions has been found, the weighted mean grain diameter $D_{m,n}$ can be calculated from the following expressions:

$$D_{4,2} = \left( \frac{\alpha \mu'_2(a)}{\beta \mu'_1(a)} \right)^{\frac{1}{2}}$$

for a relatively small depth of x-ray penetration and $$D_{6,3} = \left( \frac{\alpha \mu'_2(v)}{\beta \mu'_1(v)} \right)^{\frac{1}{3}}$$

for a relatively large depth of penetration, where $\alpha$ and $\beta$ are, respectively, equal to the diameter and volume of a grain of unit size.

In the case of a relatively small depth of x-ray penetration, the quantity $\alpha/\beta$ defines what is termed as a shape factor for unit grains of various geometries. If it is assumed that the grains are relatively equiaxed but in the shape of either a sphere, tetrahedron or cube, the shape factor $\alpha/\beta$ takes on a value of 0.524, 0.129 or 0.222, respectively.

It will be noted that the mean grain diameter $D_{m,n}$ determined in accordance with the present invention bears the subscripts m and n. These subscripts are used to denote how the mean grain size has been weighted with respect to the physical parameters of the sample population. An infinite set of averages for the value $D_{m,n}$ is defined as follows:

$$D_{m,n} = \left[ \frac{\alpha \mu'_m(D)}{\beta \mu'_n(D)} \right]^{\frac{1}{m-n}} \quad m \neq n$$

where $\mu'_z(D) = \int_0^{D_M} D^z f(D) dD$.

$\mu'_z(D)$ being the z-th statistical moment of the size distribution of grain diameter, D, and f(D)dD being the probability that a grain will be of a size $D \pm (dD/2)$, when chosen from a sample having grain diameters which vary from a minimum value of 0 to a maximum value of $D_M$. Thus $D_{2,1}$ is said to be weighted by the linear size of grains and is equal to the mean grain diameter as the term is generally used (i.e. the sum of all diameters measured divided by the total number of measurements made). $D_{6,3}$ is weighted by volume, so that the mean grain diameter which is reported is more sensitive to the occasional occurrence of large volume grains.

As mentioned, the proportionality constants $K_1$ and $K_2$ are used to relate the relative variance of the measured intensities to the ratio of the second to first statistical moments of grain volume and grain area distribution, respectively. $K_1$ and $K_2$ are therefore dependent on the operating parameters of the x-ray equipment used, as well as the physical properties of the metal sample. The following value of $K_1$ and $K_2$ have been derived and the factors comprising each constant are explained below:

$$K_1 = \frac{4\pi\mu}{jA_0\Omega\epsilon} \quad K_2 = \frac{4\pi\sin\theta}{jA_0\Omega\epsilon}$$

where
- $\mu$ = the linear absorption coefficient for the sample material
- j = multiplicity factor for the predetermined set of cystallographic diffracting planes in the sample metal chosen for measurement;
- $A_0$ = the transverse cross sectional area of the incident x-ray beam at the samples' surface;
- $\theta$ = the Bragg angle;
- $\epsilon$ = a factor to account for preferred orientation of the grains; and
- $\Omega$ = the solid angle formed from the sample to the receiving slit of the proportional counter, to account for divergence of the diffracted beam and which is estimated by $$\Omega = \frac{Zl}{4R^2\sin\theta}$$

where
- Z = the width of the receiving slit in the proportional counter;
- l = the length of the receiving slit; and
- R = distance from the sample to the receiving slit.

As is well known in the art of x-ray diffraction, a substantial amount of the time-integrated intensity measured by a proportional counter is due to background radiation. This stray radiation is produced by a number of factors including the fact that the incident x-ray beam is only substantially monochromatic. Thus, the time-integrated intensity measurements or total "counts" (designated herein as Y), must be adjusted accordingly. As mentioned, the proportional counter may be moved about the range of $2\theta \pm \Delta\theta$ in order to measure the $\Delta$-$\theta$ integrated intensity. Similarly, the counter can be moved so that the receiving slit is just outside the range of $2\theta \pm \Delta\theta$ in order to measure background radiation. With a position sensitive detector the "tails" of a peak can be seen directly. The measured intensity as represented by Y total counts is actually the sum of two contribution factors: $Y_b$, which is due to the background; and $Y_p$ which is due to the diffracted radiation in the range of $2\theta \pm \Delta\theta$. If $Y_b$ counts are measured in a time interval $\Delta t_b$ and Y counts in a time interval $\Delta t_p$ then:

$$Y = Y_p + \left( \frac{\Delta t_p}{\Delta t_b} \right) Y_b$$

and $$\sigma^2(Y) = \sigma^2(Y_p) + \left( \frac{\Delta t_p}{\Delta t_b} \right) \sigma^2(Y_b)$$

Furthermore, the variance of $Y_p$ is comprised of two factors, i.e., that due to the effect of grain size, $\sigma_{gs}^2(Y_p)$ and that due to the counting statistics, $\sigma_c^2 (Y_p)$. The counting statistics and the background intensities both follow a Poisson's distribution so that the variance of $Y_b$ and of $Y_p$ due to counting statistics is equal to the mean value of $Y_b$ and $Y_p$, respectively. Substituting these values in the previous equation yields:

$$\sigma^2(Y) = \sigma_{gs}^2(Y_p) + \overline{Y}_p + \left(\frac{\Delta t_p}{\Delta t_b}\right) \overline{Y}_b$$

The above equation divided by $\overline{Y}_p^2$ and rearranged permits the direct calculation of the relative variance of the time-integrated intensity due to the effect of grain size and is expressed:

$$\frac{\sigma^2_{gs}(Y_p)}{\overline{Y}_p^2} = \frac{\sigma^2(Y) - \overline{Y} - \left(\frac{\Delta t_p}{\Delta t_b}\right) \overline{Y}_b\left(1 + \frac{\Delta t_p}{\Delta t_b}\right)}{\left[\overline{Y} - \left(\frac{\Delta t_p}{\Delta t_b}\right) \overline{Y}_b\right]^2}$$

Thus, in accordance with a preferred form of the invention, when a proportional counter is used to measure the time integrated intensity of diffracted radiation, the receiving slit of the counter is alternately moved in and out of the range of $2\theta \pm \Delta\theta$. Generally $\Delta\theta$ is less than 2° so that the proportional counter need only be slightly displaced to measure background intensity.

Preferably, the time spent measuring background intensity is equal to the time spent measuring at or about $2\theta$. Thus, irradiated area segments $A_n$ and alternate area segments are used to measure diffracted radiation and background radiation, respectively.

In order to insure that a statistically meaningful sample has been taken of the grain population in any material, it is necessary to specify the tolerable standard error in the measurement of weighted mean grain diameter $D_{m,n}$. In, for example, drawing quality steels the permissible tolerance on grain size specification is generally $\pm\frac{1}{2}$ ASTM grain size number. The grain size for drawing quality steels varies from about $6\frac{1}{2}$ to about $8\frac{1}{2}$ ASTM grain size number so that the allowable error comprises approximately 25% of the expected range. A realistic value of the allowable tolerance in either $D_{6,3}$ or $D_{4,2}$ would therefore be about 20% and can be expressed algebraically for $D_{4,2}$, for example as:

$$\frac{\sigma(D_{4,2})}{D_{4,2}} = 0.20 = \frac{1}{2}\left(\frac{2Q}{n}\right)^{\frac{1}{2}}$$

where $$Q = 1 + \left(\frac{A}{NA_0\omega_0}\right)^2 + \frac{5}{2} \frac{nA_0\omega_0}{A}$$

and:

$$\omega_0 = \frac{\sigma^2(Y_p)}{\overline{Y}_p^2}$$

measured on a stationary specimen with an incident beam having a known transverse cross-sectional area $A_o$,
where, $W_b$ = the width of the incident beam, normal to the direction of the metal;
$V$ = velocity of the sheet;
$(t_n - t_o)$ = total time for analysis;
$A$ = the sum of the nonoverlapping area segments, $A_n$, irradiated while the counter is in the range of $2\theta \pm \Delta\theta$ and which is equal to $\frac{1}{2} W_b(t_n - t_o)$ if $\Delta t_p$ and $\Delta t_b$ are equal;
$n$ = number of overlapping area segments; and
$N$ = total number of counts registered by the proportional counter when positioned in the range of $2\theta \pm \Delta\theta$, in n subsets from n non-overlapping areas.

As previously mentioned, the counting rate of the proportional counter is directly proportional to the intensity of diffracted radiation, which in turn is dependent on the intensity of the incident beam. Thus, the intensity of the incident beam, the sensitivity of the counter, and the velocity of the sample dictate a minimum number of nonoverlapping area segments which must be irradiated in order to maintain statistical accuracy within a predetermined range. As will be shown, each of the aforementioned parameters can be directly calculated from the previous equation.

EXAMPLE

The following experiment was conducted in order to simulate the conditions which would be encountered in a temper mill when measuring grain size in accordance with the present invention. The grain size of AISI 1006 and 1008 drawing quality steels was measured both microscopically and generally in accordance with the present invention. Because the experiment was conducted under laboratory conditions it was not possible to measure the time-integrated intensities of diffracted radiation while the metal sample was in motion. The example is, however, illustrative of the application of the method and use of the apparatus of the invention.

Both the 1006 and 1008 steels had been hot rolled, coiled while hot and subsequently cold rolled to a thickness of about 0.05 inch. Both steels were then annealed at 710° C. for 60 hours in a reducing atmosphere after which they were given a final temper roll.

Several samples were cut from the 1006 sheet, mounted, polished and etched according to standard metallurgical procedures. The grain diameter of the mounted samples was determined using a microscope having a movable stage and a point inscribed on a reticule in the eyepiece. The sample was moved by the stage and as the grain boundaries crossed the inscribed point, the intercept length, L, was recorded. A total of about 1000 intercept lengths was measured on each sample, and to minimize the effect of preferred grain orientation the stage was rotated 45° after every 250 measurements. Adjacent areas of the 1006 sheet were then subjected to x-ray analysis generally in accordance with the present invention, and the mean grain size compared with the optical results. $D_{4,2}$ was determined by the optical measurements from the relationship:

$$D_{4,2} = \left[\frac{\pi a \mu_3'(L)}{3\beta\mu_1'(L)}\right]^{\frac{1}{2}}$$

and was readily obtained with the aid of a computer.

Samples were first cut from the 1008 steel for x-ray analysis, and the grain size of the actual irradiated areas was later optically determined as described above.

The grain size measurements utilizing the present invention were carried out on a General Electric diffractometer with MoK$_\alpha$ radiation ($\lambda=0.71$ Å) filtered by zirconium foil. The diffractometer was operated at 40 Kv and 7 ma for all x-ray analysis.

The depth of penetration, x, of the incident x-ray beam is a function of the Bragg angle, $\theta$, as well as the linear coefficient of absorption, $\mu$, which for a given material is a function of the x-ray wavelength. The depth of penetration is expressed as:

$$G_x = [1 - \exp(-2\mu x/\sin \theta)]$$

where $G_x$ = the fraction of diffracted intensity which is contributed by a surface layer of depth x. For 1006 and 1008 steel and using MoK$_\alpha$ radiation, $\mu$ is approximately equal to 301.2 cm$^{-1}$ and if $G_x=0.95$ is considered as corresponding to the depth of penetration, then for the eight sets of diffracting crystallographic planes in body-centered cubic iron [(110), (200), (220), (310), (222) (321) and (332)] the depth of penetration will vary from about 8.7 to 28.9 microns. This depth range is of the order of the expected grain size or less so that the relative variance in time-integrated diffracted radiation is given by:

$$\frac{\sigma_{gs}^2(Y_p)}{\overline{Y}_p^2} = \frac{4\pi\sin\theta}{jA_0\Omega\epsilon} \frac{\mu'_2(a)}{\mu'_1(a)}$$

and the weighted mean grain diameter $D_{4,2}$ is given by:

$$D_{4,2} = \left[\left(\frac{jA_0\omega\epsilon\alpha}{4\pi\beta\sin\theta}\right)\left(\frac{\sigma_{gs}^2(Y_p)}{\overline{Y}_p^2}\right)\right]^{\frac{1}{3}}$$

which is also readily calculable on the computer.

For purposes of the present experiment a random grain orientation was assumed so that $\epsilon=1$, and the shape of the grains was assumed to be spherical so that $\alpha/\beta=0.524$.

The optically determined mean grain diameter $D_{4,2}$ for the 1006 steel varied from about 45.4 to about 51.5 microns, which compares favorably to $D_{4,2}$ determined by the time- and $\Delta\theta$-integrated intensity of diffracted radiation from various diffracting planes as shown in Table I. While only the front reflection of the Debye-Scherrer cone is shown in FIG. 1, a symmetrical but weaker back reflection cone is also formed and may be used to determine grain size in accordance with the invention and is reported in Table I.

On the 1008 sample the optically determine $D_{4,2}$ varied from about 47.9 to about 54.2 microns. The time-integrated peak intensity (i.e. the proportional counter positioned precisely at $2\theta$) was measured for various diffracting planes and used to determine $D_{4,2}$ in accordance with the invention. These results, set forth in Table II also compare very favorably with the optical measurements.

In accordance with the present invention the time-integrated peak intensity data obtained from the front reflection of the (211) diffracting planes in the 1008 sample was used as a model to determine the limiting parameters for a standard error of 20% in grain size measurement if the sheet was traveling at a velocity of 1500 ft./min. The incident x-ray beam had a transverse cross sectional area of 0.8125 cm.$^2$ and a width of 1 cm.

Assuming a total analysis time of 10 seconds, the total irradiated area is equal to 7,620 cm$^2$. The relative variance in the counts $Y_p$ due to grain size on the stationary sample was found to be $5.69 \times 10^{-13}$. Substituting these values into the previously explained equation for standard error in a moving sample, it is possible to solve directly for n and thus determine the minimum number of area segments for a given counting rate which is necessary to measure grain size within the desired accuracy. In order to maintain a standard error of 20% or less, it was found that at least 13 area segments had to be measured on the 1008 sheets with a corresponding counting rate of $4.96 \times 10^7$ counts per minute. It will be understood by those skilled in the art that if the total irradiated area is further subdivided into a greater number of smaller area segments, then the desired accuracy can be maintained with a lower counting rate.

TABLE I $D_{4,2}$ (Microns) Determined by X-Ray Analysis on 1006 Steel

| Reflections | Diffracting Planes | | | | | | | |
|---|---|---|---|---|---|---|---|---|
| | 110 | 200 | 211 | 220 | 310 | 222 | 321 | 332 |
| Front | 50.4 | 53.1 | 35.5 | 58.0 | 60.7 | 30.2 | 34.9 | 28.1 |
| Back | 108.6 | 59.7 | 56.3 | 64.5 | 79.2 | 38.9 | 29.0 | 38.5 |
| Both | 93.3 | 54.2 | 46.8 | 60.7 | 77.3 | 31.3 | 31.7 | 32.1 |

TABLE II $D_{4,2}$ (Microns) Determined by X-Ray Analysis on 1008 Steel using Peak Intensity Measurements

| Reflection | Diffracting Planes | | | | | |
|---|---|---|---|---|---|---|
| | 211 | 220 | 310 | 222 | .321 | 332 |
| Front | 40.5 | 30.7 | 29.8 | 14.5 | 41.6 | 32.6 |

Thus, if the total irradiated area is subdivided into 100 area segments the corresponding minimum counting rate for a 20% standard error is $3.74 \times 10^6$ counts per minute.

If an oxide layer is present over a metal sample, as could readily occur under certain conditions such as hot rolling, then the intensity of the incident x-ray beam can be increased in order to sufficiently penetrate the underlying metal and carry out the desired grain size measurements. This technique can also be used to obtain information on the thickness and grain size of the oxide layer itself by monitoring oxide diffraction peaks.

Penetration depths based on $G_x=0.95$ are shown below for FeO and Fe$_2$O$_3$ at values of $\theta$ corresponding to five different diffracting planes in body centered cubic iron.

| Diffracting Plane | Penetration depth, microns ($G_x = .95$) | |
|---|---|---|
| | FeO | Fe$_2$O$_3$ |
| 110 | 15 | 18.4 |
| 220 | 30.6 | 36.9 |
| 222 | 37.5 | 45.2 |
| 332 | 50.6 | 61.0 |

Thus, with the intensity of incident MoK$_\alpha$ radiation used in the foregoing experiment, surface scale thicker than about 0.002 inch would prevent accurate measurement. However, the intensity of the incident x-radiation produced by an x-ray tube is readily increased so that absorption by the scale can easily be overcome.

In another embodiment in order to attain a greater depth of penetration a shorter x-ray wavelength can be used, such as $WK_\alpha=0.21$ Å or $AgK_\alpha=0.56$ Å. Similarly, to attain a lesser depth of penetration, a longer wavelength can be used, such as $C_rK_\alpha=2.29$ Å. Any one of a large number of target materials can be used to produce a set of suitable $K_\alpha$ x-radiation beams, such as Ti, V, Cr, Mn, Fe, Co, Ni, Ca, Zn, Al, Mo, W, Ta and Ag. Furthermore, one can use two or more x-ray beams with different wavelengths to penetrate a range of depths in the material simultaneously. In such an embodiment preferably the two or more x-ray beams are monochromatic $K_\alpha$ beams and the beams are directed to irradiate substantially the same area segments on the material. Therefore, by using two or more beams, by varying the x-ray intensities and by measuring diffracted intensities from a range of crystallographic planes, a broad range of depths can be penetrated for measurement of grain size. Such a technique could be of use for materials having a grain size gradient or for multilayer materials, such as clad metals and semiconductor substrates composed of a plurality of layers.

Although certain preferred embodiments of the present invention have been illustrated and described herein, other embodiments will become apparent to those skilled in the art and, accordingly, the scope of the present invention should be defined only by the following claims.

What is claimed is:

1. A method for on-line measurement and process control of grain size at a plurality of depths in a material comprising the steps of:
   traveling the materials and a predetermined measuring station relative to one another;
   directing a plurality of incident beams, each incident beam comprising substantially monochromatic x-radiation and each incident beam having a unique wavelength, at the material as the measuring station and the material travel relative to one another, said incident beams having a predetermined transverse cross-sectional area so that over a plurality of time intervals the incident beams concurrently trace a plurality of substatially the same non-overlapping irradiated area segments;
   detecting a time integrated intensity of diffracted radiation corresponding to a predetermined set of crystallographic planes over a range of depths of the material for each of the area segments on the material;
   determining a relative variance of the time integrated intensity diffracted from the plurality of non-overlapping irradiated area segments for each unique beam wavelength;
   determining a mean diameter for the grains at a plurality of depths using the relative variance of the integrated intensity;
   varying at least one process parameter in response to the determined mean grain diameter of at least one depth to control grain size for at least one depth.

2. The method of claim 1 wherein the predetermined measuring station travels while the material remains fixed.

3. The method of claim 1 wherein the material travels while the predetermined measuring station remains fixed.

4. The method of claim 1 further characterized in that said material is a material having a grain size gradient and the step of varying comprises controlling the grain size gradient responsive to determinations of the mean grain diameter.

5. The method of claim 4 further characterized in that said material having a grain size gradient is a substantially polycrystalline material selected from the group consisting of metals, clad metals, single and multilayer semiconductors, polymers, minerals and ceramics.

6. The method of claim 1 wherein each said incident beam has a variable intensity magnitude which enables determination of the mean grain diameter in said material for a further range of depths.

7. The method of claim 6 wherein said incident beams comprise a $a_\alpha MoK_\alpha$ x-radiation beam and a $WK_\alpha$ x-radiation beam.

8. The method of claim 6 further including the step of determining a shape characteristic for the grains by means of the diffracted x-rays from the material.

9. The method of claim 6 wherein each said incident beam has an associated means for detecting said time integrated intensity.

10. The method of claim 9 wherein said means for detecting comprises a proportional counter.

11. The method of claim 9 wherein said means for detecting comprises a position sensitive detector.

12. The method of claim 11 wherein said counter is alternately positioned within the range of $2\theta \pm \Delta\theta$ for a time $t_p$, the time integrated intensity being measured in counts Y, and outside the range of $2\theta \pm \Delta\theta$ for a time $t_d$ to measure background radiation in counts $Y_b$ in order to determine the true intensity of diffracted radiation in counts $Y_p$.

13. Apparatus for on-line measurement and process control of grain size in materials comprising:
   means for traveling the material relative to a predetermined measuring station;
   means for irradiating the traveling material with a plurality of incident beams, each said incident beam comprising substantially monochromatic x-radiation and each incident beam having a unique wavelength, said incident beams having a predetermined transverse cross-sectional area so that over a plurality of time intervals the incident beams concurrently trace a plurality of substantially the same non-overlapping irradiated area segments;
   means for measuring a time integrated intensity of x-radiation diffracted by said material and corresponding to a predetermined set of crystallographic planes over a range of depths of the material for each of the area segments on the material;
   means associated with said measuring means for determining a relative variance of said time integrated x-ray intensity measurements corresponding to the plurality of non-overlapping area segments for each unique beam wavelength;
   means for determining a mean diameter for the grains at a plurality of depths responsive to the relative variance;
   means for controlling at least one process parameter in response to the mean grain diameter of at least one depth to control grain size for at least one depth.

14. The apparatus of claim 13 wherein said material has a grain size gradient and wherein the means for controlling controls the grain size gradient responsive to determination of mean grain diameter.

15. The apparatus of claim 14 further characterized in that said incident x-radiation beams comprise at least two monochromatic $K_\alpha$ x-radiation beams.

16. The apparatus of claim 15 wherein the means for irradiating is further characterized in that said monochromatic $K_\alpha$ x-radiation beams have variable intensity magnitude which enable determination of mean grain diameter for a further range of depths.

17. The apparatus of claim 15 wherein said at least two monochromatic $K_\alpha$ x-radiation beams are produced from targets selected from the group consisting of W, Mo, Ta, Ag, Ti, V, Cr, Mn, Fe, Co, Ni, Cu, Zn, and Al.

18. The apparatus of claim 15 wherein said at least two monochromatic x-radiation beams comprise $AgK_\alpha$ and $MoK_\alpha$.

19. The apparatus of claim 15 wherein said at least two monochromatic x-radiation beams comprise $MoK_a$ and $WK_\alpha$.

* * * * *